United States Patent [19]
Hoffmann et al.

[11] 3,996,246
[45] Dec. 7, 1976

[54] RESOLUTION OF RACEMIC PANTOLACTONE

[75] Inventors: Werner Hoffmann, Neuhofen; Walter Himmele, Walldorf; Joachim Paust, Neuhofen; Karl Von Fraunberg, Bad Duerkheim; Hardo Siegel, Ludwigshafen; Sigberg Pfohl, Speyer, all of Germany

[73] Assignee: BASF Aktiengesellschaft, Ludwigshafen (Rhine), Germany

[22] Filed: Jan. 24, 1975

[21] Appl. No.: 543,695

[30] Foreign Application Priority Data

Jan. 30, 1974  Germany ........................ 2404305
Nov. 9, 1974  Germany ........................ 2453283

[52] U.S. Cl. ........................ 260/343.6; 260/535 R; 260/563 R
[51] Int. Cl.² ........................ C07D 307/32
[58] Field of Search .................... 260/343.6, 535 R

[56] References Cited

UNITED STATES PATENTS 2,319,545  5/1943  Harris et al. ........................ 260/284

*Primary Examiner*—Henry R. Jiles
*Assistant Examiner*—C. M. S. Jaisle
*Attorney, Agent, or Firm*—Johnston, Keil, Thompson & Shurtleff

[57] ABSTRACT

A process for resolving racemic α-hydroxy-β,β-dimethyl-γ-butyrolactone, referred to as D,L-pantolactone, into its optical antipodes, based on the separation of diastereomeric salts of D,L-pantoic acid (α,γ-dihydroxy-β,β-dimethylbutyric acid), produced from D,L-pantolactone, by means of (—)-3-aminomethylpinane, (+)-3-aminomethylpinane or one of their acid addition salts, as a new resolving agent.

2 Claims, No Drawings

RESOLUTION OF RACEMIC PANTOLACTONE

The present invention relates to a process for resolving racemic α-hydroxy-β,β-dimethyl-γ-butyrolactone, referred to as D,L-pantolactone, into its optical antipodes and is based on the separation of diastereomeric salts of D,L-pantoic acid (α,β-dihydroxy-β, β-dimethylbutyric acid), produced from D,L-pantolactone, by means of (−)-3-aminomethylpinane, (+)-3-aminomethylpinane or one of their acid addition salts, as a new resolving reagent.

D(−)Pantolactone, required, e.g., for the synthesis of D-(+)-pantothenic acid, D-(+)-panthenol and D-(+)-panthetin can be obtained in various ways by resolution of racemic pantolactone.

Most of the conventional processes are based on separating the diastereomers of derivatives of racemic pantolactone with optically active auxiliaries.

The methods suitable for industrial resolution of racemic D,L-pantolactone are based on converting racemic pantolactone into diastereomeric salts of α,γ-dihydroxy-β,β-dimethylbutyric acid with suitable optically active amines. After fractional crystallization of the diastereomers, the salt of the desired optical antipode is reconverted to the lactone. This method has been described, e.g., in U.S. Pat. No. 2,319,545, using quinine, and in East German Pat. No. 32,628, using L-(+)-1-(p-nitrophenyl)-2-amino-1,3-propanediol.

Quinine has the disadvantages that it is a very expensive substance and has a high molecular weight; its price is greatly subject to market fluctuations, and the compound is at times difficult to obtain. The disadvantages of L-(+)-1-(p-nitrophenyl)-2-amino-1,3-propanediol are, inter alia, that like quinine it is not always available in sufficient amount.

A recently disclosed process for resolving racemic pantolactone is based on separating the diastereomers of the salts of α,γ-dihydroxy-β,β-dimethylbutyric acid, referred to as pantoic acid, with dehydroabietylamine, and is described in German Pat. No. 1,568,755. However, dehydroabietylamine is also relatively difficult to obtain. Abietic acid, the starting material for dehydroabietylamine, is a constituent of rosin, which does occur in sufficient quantity in nature; however, the manufacture of pure dehydroabietylamine, as required for the resolution of racemic pantolactone, is rather expensive.

By way of example, the dehydroabietylamine is prepared as follows: rosin is subjected tp a treatment with acid or caustic alkali, described as an isomerization, which first gives abietic acid, which is then converted to dehydroabietic acid by disproportionation. The dehydroabietic acid is then converted to the acid amide, which is converted to the nitrile by elimination of water. Finally, this nitrile must be reduced to the amine, namely dehydroabietyamine.

A further disadvantage of using dehydroabietylamine to resolve racemic pantolactone is the relatively high molecular weight of dehydroabietylamine, which requires large quantities of the optically active auxiliary to be employed and recovered. A further disadvantage is that when separating the diastereomers the desired D-(−)-pantolactone remains in solution and must be isolated from the crystallization mother liquors, whilst the biologically inactive form, L-(+)-pantolactone, is obtained as the sparingly soluble diastereomer from the crystal fractions, which are usually obtained in a very pure form. It would be more advantageous if the desired optically active form could be obtained from the less soluble diastereomer, which crystallizes out first.

We have now found a process for resolving racemic pantolactone by separating diastereomeric salts of pantoic acid, on which pantolactone is based, wherein the resolution is carried out by means of (+)-3-aminomethylpinane, (−)-3-aminomethylpinane or one of their acid addition salts.

(−)- and (+)-3-aminomethylpinane are optically active amines which have not previously been described. Their structural formulae are illustrated below.

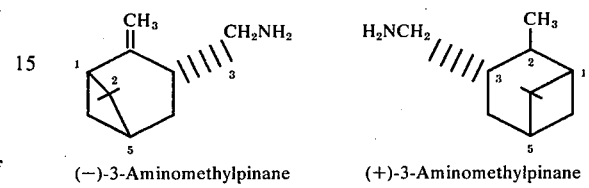

(−)-3-Aminomethylpinane     (+)-3-Aminomethylpinane (−)- and (+)-3-aminomethylpinane can be obtained simply, and in high yields, from (+)-α-pinene and (−)-α-pinene, respectively, by a method which entails only two reaction steps, namely hydroformylation and reductive amination. It should be pointed out that the manufacture of optically active aminomethylpinanes forms the subject of U.S. patent application Ser. No. 544,306, filed Jan. 27, 1975, "Optically Active Pinane Derivatives". E.g., (+)-α-pinene can be obtained in large quantities and high optical purity from turpentine oil or juniper oil.

Racemic pantolactone can be resolved into its optical antipodes, of high purity, with excellent yields by the process according to the invention since, surprisingly, there is a considerable difference in solubility between the salts of (−)- or (+)-3-aminomethylpinane with D- and L-pantoic acid respectively. The invention provides industry with a new process for resolving racemic pantolactone. A particularly marked advantage of using (+)-3-aminomethylpinane for resolving D,L-pantolactone is the low molecular weight, as a result of which the amounts of optically active auxiliary which have to be employed are relatively small. It is surprising, and particularly advantageous, that when using (+)-3-aminomethylpinane for resolving the racemate, the diastereomeric salt of D-pantoic acid and (+)-3-aminomethylpinane precipitates in pure crystalline form. The desired D-pantolactone can be isolated in a crystalline form from this crystal fraction.

If (−)-3-aminomethylpinane is used, the diastereomeric salt of (−)-3-aminomethylpinane with L-pantoic acid precipitates in an almost pure crystalline form on mixing aqueous or aqueous-alcoholic, especially aqueous-methanolic, solutions of sodium DL-pantoate and (−)-3-aminomethylpinane hydrochloride. The desired D-pantolactone is obtained from the mother liquor in an optically pure, crystalline form.

The low boiling point of (−)- and (+)-3-aminomethylpinane, namely 110° C at 20 mm Hg, is a great technical advantage since the optically active base used can be purified and recovered simply by distillation.

The process is generally carried out as follows: first, racemic pantolactone is converted into the alkali metal salt of racemic pantoic acid by means of an equivalent quantity of alkali metal hydroxide, especially sodium hydroxide, in aqueous solution, preferably by heating the aqueous solution of the pantolactone at from 50 to 100° C for from 20 minutes to 2 hours. The resulting solution of the alkali metal salt of DL-pantoic acid is then preferably mixed with on equivalent of an acid addition salt of (−)- or (+)-3-aminomethylpinane, suitable temperatures being from 0° to 90° C, preferably from 40° to 60° C.

The acid addition salts used are salts of strong inorganic acids, for example halides, especially chlorides and bromides. However, nitrates, phosphates and salts of organic acids, especially acetates, can also be used. Preferably, the strength of the pantolactone solutions used is from 5 to 40 percent by weight.

The acid addition salt is added as a solid or, preferably, as a solution in a solvent, preferably in water. Other solvents which can be used, and which should be water-miscible, are lower alcohols such as methanol or ethanol, acetone, nitriles, such as acetonitrile, and acid amides, such as dimethylformamide, especially in the form of mixtures with water. In general, the strength of the solutions of the acid addition salt is from 5 to 25 percent by weight. If an aqueous alcohol is used as the solvent, the proportion of alcohol may be up to 60% by weight, and is preferably from 30 to 50% by weight.

The diastereomeric salts of D- and L-pantoic acid and of (−)- or (+)-3-aminomethylpinane are produced by an exchange reaction; the sparingly soluble D-pantoate of (+)-3-aminomethylpinane or L-pantoate of (−)-3-aminomethylpinane crystallizes out from the solution and can be separated by filtration from the readily soluble salt left in the mother liquor.

The D-pantoate of (+)-3-aminomethylpinane or L-pantoate of (−)-3-aminomethylpinane, which has been filtered off, is dissolved or suspended in water and treated with a sufficient quantity of alkali metal hydroxide, for example sodium hydroxide solution, by customary methods. The purity of the salt which has been filtered off can be improved by re-suspending the crystals in water, stirring vigorously for about 10 minutes and filtering the crystals off again. The (−)- or (+)-3-aminomethylpinane can be recovered by extraction with an organic solvent, for example ether or methylene chloride. Thereafter, the aqueous phase is acidified, preferably with hydrochloric acid or sulfuric acid, to pH 1 to cause the lactone to form, and after completion of this reaction, which as a rule has occurred after standing for two hours at room temperature, the D-(−)-pantolactone is extracted with organic solvents, such as methylene chloride or ether.

The solution of L-pantoate of (+)-3-aminomethylpinane can be treated with alkali in the same way, so that the remaining (+)-3-aminomethylpinane is recovered, whilst after acidification L-(+)-pantolactone can be obtained.

L-(+)-Pantolactone can be racemized by conventional methods and the racemate can be recycled to the process.

The sodium L-pantoate can also simply be racemized directly in solution, without isolating the L-(+)-pantolactone.

The desired D-pantolactone can easily be isolated from the solution of the D-pantoate of (−)-3-aminomethylpinane, and can easily be purified. First, an at least equivalent amount of a strong base, for example sodium hydroxide solution, is added; the (−)-3-aminomethylpinane liberated is isolated by extraction with an organic solvent, for example ether or benzene, and the aqueous alkaline solution is then acidified with concentrated hydrochloric acid or sulfuric acid. This first liberates D-pantoic acid, which rapidly cyclizes to D-(−)-pantolactone and can be extracted from the aqueous salt solution by means of organic solvents, such as methylene chloride or ether.

The crystalline L-pantoate of (−)-3-aminomethylpinane can be treated analogously with aqueous alkali to decompose it to (−)-3-aminomethylpinane and L-pantolactone, thereby obtaining both the remaining (−)-3-aminomethylpinane and also L-pantolactone which can be racemized by conventional methods and recycled to the process.

The resolution of the racemate by means of (−)- or (+)-3-aminomethylpinane, in accordance with the invention, can be effected particularly advantageously by mixing the alkali metal salt of D,L-pantoic acid with only half an equivalent of the acid addition salt of (−)-3-aminomethylpinane or of (+)-3-aminomethylpinane. Hereupon, the sparingly soluble diastereomeric L-pantoate of (−)-3-aminomethylpinane or D-pantoate of (+)-3-aminomethylpinane crystallizes out, whilst D-pantoic acid or L-pantoic acid remains in solution as the alkali metal salt. This process is preferably carried out using a molar ratio of from 1 : 0.5 to 1 : 0.7. After filtration, the filtrate is acidified as described above and D-(−)- or L-(+)-pantolactone is isolated therefrom by extraction with organic solvents. The concentrations used are analogous to the conditions described above.

The alkali metal salt of L-pantoic acid, which has remained in the filtrate, can be racemized directly, without conversion to L-(+)-pantolactone, and can then be reused in the racemate resolution process.

The D- pantoate of (+)-3-aminomethylpinane which has precipitated is decomposed with alkali metal hydroxides, the (+)-3-aminomethylpinane is extracted from the alkaline medium by means of organic solvents, and the aqueous phase is acidified.

After completion of the lactone formation, the D-(−)-pantolactone is extracted with organic solvents.

The optically active bases (+)- and (−)-3-aminomethylpinane prove astonishingly stable in the course of the various stages of the process. In none of them are measurable quantities of by-products produced, so that when recycling the (+)- or (−)-3-aminomethylpinane and L-pantolactone for re-use, neither the 3-aminomethylpinane nor the racemized pantolactone has to be subjected to special purification treatments. The optical purity of the D-pantolactone obtained in accordance with the process corresponds, within the limits of analytical error, to the data given in Example 3 for the product obtained from a first separation, even after the optically active base used, the racemized pantolactone left in each case, and the solvent used, have been recycled 20 times; this shows that special purification treatments are not necessary. The new process gives optically pure D-(−)-pantolactone in an overall yield of 90%, based on the DL-pantolactone employed.

EXAMPLE 1 a. (+)-3-Formylpinane 500 ml (428 g) of (−)-α-pinene of optical rotation $[\alpha]_D^{20} = -35.8°$ (pure, 1 dm) and 250 mg of dimeric rhodium-1,5-cyclooctadienyl chloride are introduced into a one liter high-pressure vessel. After displacing the air with an equimolar mixture of carbon monoxide and hydrogen, the pressure is raised to 100 atmospheres and the reaction mixture is then heated to 110° C; a pressure of 650 atmospheres is maintained over 6 hours by replenishing the said gas mixture. After cooling, and releasing the pressure, a reaction mixture which, according to analysis by gas chromatography, consists of 11% by weight of (−)-α-pinene, 61 percent by weight of optically active 3-formylpinane and 26 percent by weight of the structurally isomeric aldehyde is obtained. This mixture is freed from the catalyst by molecular distillation under reduced pressure. The distillate is then fractionally distilled in a column with 20 perforated plates, using a reflux ratio of 1 : 5. 285 g of (+)-3-formylpinane of $[\alpha]_D^{23} = +19.17°$ (pure) are obtained at from 103° to 104° C at 18 mm Hg. The yield of (+)-3-formylpinane is 52% of theory, based on (−)-α-pinene.

b. (−)-3-Formylpinane 3,000 g (approx. 3.5 l) of (+)-α-pinene, of optical rotation $[\alpha]_D^{23} = +38.0°$ (pure), and 1 g of dimeric rhodium-1,5-cyclooctadienyl chloride [RhClCOD]$_2$ are heated to 70° C in an autoclave which has a reaction space of 10 liters and is fitted with a magnetically reciprocated stirrer; the reaction is carried out under a pressure of 650 bars with a mixture of carbon monoxide and hydrogen in the ratio of 1:1 by volume. The pressure is maintained for 36 hours by replenishing the gas mixture. After completion of the reaction, the mixture is allowed to cool under pressure, and the autoclave is then opened. A reaction mixture which, according to analysis by gas chromatography, consists of 15.5% of 60 -pinene, 1% of β-pinene, 72.1% of (−)-3-formylpinane and 10.4% of isomeric aldehydes is obtained. The reaction mixture is worked up by fractional distillation. The resulting structurally pure (−)-3-formylpinane (of which 1,810 g are obtained) has an optical rotation of $[\alpha]_D^{23} = -23.1°$ (pure) and boils at 77° C at 5 mm Hg.

EXAMPLE 2 a. (+)-3-Aminomethylpinane and (+)-3-aminomethylpinane hydrochloride 300 g of ethanol and 50 g of Raney cobalt are introduced into a high pressure vessel of 2.5 liters capacity and the air is removed by flushing with nitrogen. 400 g of liquid ammonia are then introduced, followed by hydrogen until the total pressure is 50 atmospheres. The reaction mixture is then heated to 80° C and the pressure is set to 150 atmospheres with hydrogen. 200 g of (+)-3-formylpinane are introduced in the course of 6 hours, and after a further 2 hours the reaction mixture is cooled and the pressure is released. 650 g of a mixture, fractional distillation of which gives 106 g of (+)-3-aminomethylpinane boiling at from 110° to 111° C at 200 mm Hg, are obtained.

120 g of the 3-aminomethylpinane thus obtained are dissolved in 1.3 l of pentane and dry hydrogen chloride is passed into the solution at from 0° to 5° C, whilst stirring. When free amine is no longer detectable, the crystals produced are filtered off and dried. 142 g of (+)-3-aminomethylpinane hydrochloride of optical rotation $[\alpha]_D^{23} = +35.4°$ (c = 1, methanol) are obtained.

118 g of (+)-3-aminomethylpinane hydrochloride, which has an optical rotation of $[\alpha]_D^{23} = +35.4°$, are recrystallized from butyl acetate/ethanol. 85 g of (+)-3-aminomethylpinane hydrochloride of optical rotation $[\alpha]_D^{23} = +40.5°$ are obtained. A further 29 g of specific optical rotation $[\alpha]_D^{23} = 17.3°$ are obtained from the mother liquor. The salt of optical rotation $[\alpha]_D^{23} = +40.5°$ is recrystallized once more from butyl acetate/ethanol, giving 70 g of (+)-3-aminomethylpinane hydrochloride of specific optical rotation $[\alpha]_D^{23} = +44.3°$.

On recrystallizing 30 g of (+)-3-aminomethylpinane hydrochloride of optical rotation $[\alpha]_D^{23} = +35.4°$ three times from a mixture of ethyl acetate and methanol, a (+)-3-aminomethylpinane hydrochloride of specific optical rotation $[\alpha]_D^{23} = +44.7°$ is obtained.

b. (−)-3-Aminomethylpinane 150 g of Raney cobalt, suspended in 1,000 ml of ethanol and 3.5 kg of ammonia, are heated to 80° C in a stirred autoclave, and hydrogen is then introduced until the total pressure is 150 bars. 2,020 g of (−)-3-formylpinane are pumped in over 6 hours. The pressure is kept constant by replenishing with hydrogen. After completion of the reaction, the autoclave is allowed to cool and the pressure is then released. The reaction product, weighing 3,450 g, is worked up by fractional distillation, giving 1,450 g of structurally pure (−)-3-aminomethylpinane, which boils at 100° C at 11 mm Hg and has an optical rotation of $[\alpha]_D^{23} = -32.6°$ (pure).

(−)-3-Aminomethylpinane hydrochloride 100 g of (−)-3-aminomethylpinane of $[\alpha]_D^{23} = -32.6°$ (pure), 100 ml of methanol and 500 ml of butyl acetate are introduced into a 1—1 three-necked flask, and dry HCl gas is stirred into the liquid at an internal temperature of from 0° to 5° C. (−)-3-Aminomethylpinane hydrochloride precipitates. When the precipitation has ceased, 25 ml of methanol are added and the mixture is heated under reflux for 1 hour and then cooled to 0° C. The crystals which have precipitated are filtered off, washed with 100 ml of cold butyl acetate and dried, giving 91 g of (−)-3-aminomethylpinane hydrochloride of $[\alpha]_D = -44.0°$ (c = 4, CH$_3$OH). An (−)-3-aminomethylpinane of $[\alpha]_D^{23} = -39.6°$ (pure) can be obtained from the hydrochloride by reaction with aqueous sodium hydroxide solution, extraction with ether and subsequent distillation.

EXAMPLE 3

32.5 parts of D,L-pantolactone are added to a solution of 10 parts of sodium hydroxide in 100 parts of water. The mixture is heated at 80° C for 30 minutes, resulting in the formation of racemic sodium pantoate. The pH of the solution is adjusted to 8.5 by adding 2 N hydrochloric acid. A solution of 24.5 parts of (+)-3-aminomethylpinane hydrochloride ($[\alpha]_D^{20} = +43.1°$, 1% in methanol) in 150 parts of water is added to the solution in the course of 10 minutes at room temperature, whilst stirring, resulting in the immediate precipitation of a thick crystal mush. After stirring for two hours at room temperature, the suspension is cooled to 0° C and the mush is filtered off and washed twice with a little cold water. After drying the crystals, 38.6 parts of the D-pantoate of (+)-3-aminoethylpinane are obtained (98% yield; $[\alpha]_D^{20} = +40.3°$, 1% in methanol).

The filtrate is rendered alkaline with dilute sodium hydroxide solution and is briefly shaken with 50 parts of ether to extract traces of unreacted (+)-3-aminomethylpinane.

The filtrate containing sodium L-pantoate is acidified to pH 1 with half-concentrated sulfuric acid. After standing for 2 hours at room temperature, L-(+)-pantolactone has been formed. The acid solution is saturated with sodium chloride and the L-(+)-pantolactone is then extracted continuously for 12 hours by means of ether, in an extraction apparatus.

On concentrating the ether extract, 15.5 parts of L-(+)-pantolactone are obtained (95% yield; $[\alpha]_D^{20} = +38.0°$, 1% in water).

Recrystallization from 60 parts of diisopropyl ether gives 13 parts of pure L-(+)-pantolactone in a yield of 80%, based on racemic pantolactone employed ($[\alpha]_D^{20} = 48.9°$, 1% in water).

The D-pantoate of (+)-3-aminomethylpinane, which has crystallized out, is now suspended in 200 parts of water and 200 parts of ether and the suspension is rendered alkaline with concentrated sodium hydroxide solution. The (+)-3-aminomethylpinane liberated is transferred to the ether phase by vigorous shaking and after separating off the aqueous phase the (+)-3-aminomethylpinane is recovered by concentrating the ether extract. 19.5 parts of (+)-3-aminomethylpinane (94% of the amount initially employed) are recovered. The amine is quantitatively reconverted to the hydrochloride ($[\alpha]_D^{20} = 42.9°$, 1% in methanol) by dissolving in n-pentane and passing hydrogen chloride into the solution, and can be re-used to resolve the racemate.

The aminomethylpinane can also be recovered as crystalline acetate by simply adding the stoichiometric amount of glacial acetic acid to the solution of the (+)-3-aminomethylpinane in ether, the acetate precipitating immediately. The acetate can be filtered off ($[\alpha]_D^{20} = +32°$, 1% in methanol) and then be re-used to resolve the racemate.

After having removed the ether phase, the D-pantolactone is obtained from the aqueous phase by acidifying the aqueous phase with half-concentrated sulfuric acid (pH = 1), allowing it to stand for two hours at room temperature, saturating with sodium chloride, and extracting continuously for 12 hours with ether in an extraction apparatus.

On concentrating the ether extract, 15.3 parts of D-(−)-pantolactone (94% yield, based on D-pantolactone; $[\alpha]_D^{20} = 38.6°$, 1% in water) are obtained. Recrystallization from 30 parts of diisopropyl ether gives 13.1 parts of pure D-(−)-pantolactone in a total yield of 81%, based on racemic pantolactone initially employed ($[\alpha]_D^{20} = -49.8°$, 1% in water).

EXAMPLE 4

26 parts of pantolactone are added to a solution of 8 parts of sodium hydroxide in 80 parts of water, and the mixture is heated to 80° C for 20 minutes.

The solution is brought to pH 8.5 with dilute hydrochloric acid and a solution of 26.4 parts of the acetate of (+)-3-aminomethylpinane ($[\alpha]_D^{20} = +32°$, 1% in methanol), in 100 parts of water, is then added dropwise in the course of 10 minutes at room temperature, whilst stirring.

After stirring for two hours, the mixture is cooled to 0° C and the precipitate which has formed is filtered off and washed with a little cold water. 29 parts of the D-pantoate of (+)-3-aminomethylpinane (92% yield, based on D-pantolactone; $[\alpha]_D^{20} = +42.8°$, 1% in methanol) are obtained.

The filtrate is acidified with concentrated sulfuric acid, and after standing for 2 hours and saturating with sodium chloride the L-(+)-pantolactone is extracted with ether in an extraction apparatus. On concentrating the ether extract, 13.0 parts of L-(+)-pantolactone are obtained (100%; $[\alpha]_D^{20} = +27.8°$, 1% in water).

The D-pantoate of (+)-3-aminomethylpinane is suspended in 100 parts of water and 200 parts of ether and the suspension is rendered alkaline with sodium hydroxide solution. The ether phase is separated off and the (+)-3-aminomethylpinane is recovered from it.

The aqueous phase is acidified with sulfuric acid, and after saturation with sodium chloride the D-(−)-pantolactone is extracted with ether in an extraction apparatus.

On concentrating the ether extract, 12 parts of D-(−)-pantolactone are obtained (92%, based on D-pantolactone; $[\alpha]_D^{20} = -39.2°$, 1% in water). Recrystallization from 25 parts of diisopropyl ether gives 9.7 parts of optically pure D-(−)-pantolactone in a total yield of 75%, based on D,L-pantolactone initially employed ($[\alpha]_D^{20} = 0 -50.2°$, 1% in water).

EXAMPLE 5

3.25 parts of D,L-pantolactone are added to a solution of 1 part of sodium hydroxide in 50 parts of water and the mixture is heated at from 80° to 90° C for 20 minutes.

The solution is adjusted to pH 8.5 and 5.05 parts of (+)-3-aminomethylpinane hydrochloride ($[\alpha]_D^{20} = +43°$, 1% in methanol) are added in portions, at room temperature. After 10 minutes a precipitate forms which is filtered off after standing for 10 hours at room temperature and dried.

4.0 parts of the D-pantoate of (+)-3-aminomethylpinane are obtained (100%; $[\alpha]_D^{20} = +38.8°$, 1% in methanol).

The filtrate, containing the dissolved L-pantoate of (+)-3-aminomethylpinane, is rendered alkaline with sodium hydroxide solution and the (+)-3-aminomethylpinane is recovered with 20 parts of ether. The aqueous phase is acidified with sulfuric acid and after one hour at room temperature is extracted with five times 20 parts of methylene chloride. The combined methylene chloride extracts are concentrated, giving 1.25 parts of L-(+)-pantolactone (77%; $[\alpha]_D^{20} = +30°$, 1% in water). The crystals of the D-pantoate of (+)-3-aminomethylpinane are suspended in 20 parts of water and 20 parts of ether and the mixture is rendered alkaline with sodium hydroxide solution. (+)-3-Aminomethylpinane is recovered from the ether phase. The aqueous phase is acidified and is extracted with five times 20 parts of methylene chloride when the formation of the lactone is complete.

On concentrating the methylene chloride, 1.4 parts of D(−)-pantolactone (86%; $[\alpha]_D^{20} = -31°$, 1% in water) are obtained. When this is recrystallized from a mixture of tert.-butanol and petroleum ether, D-(−)-pantolactone is obtained in a total yield of 62% ($[\alpha]_D^{20} = -48.6°$, 1% in water).

EXAMPLE 6

130 g (1 mole) of DL-pantolactone are dissolved in 300 ml of water, and the solution is heated to 80° C in a 2-1 four-necked flask equipped with a stirrer, thermometer, reflux condenser and 500 ml dropping funnel. 100 g (1 mole) of a 40% strength aqueous sodium hydroxide solution are added dropwise to the above solution in the course of 20 minutes, and the mixture is then stirred for 10 minutes at 80° C. If necessary, the pH of this solution is adjusted to 8.8 by dropwise addition of 1 N hydrochloric acid or 40% strength sodium hydroxide solution (this pH corresponds to that of a concentrated aqueous sodium pantoate solution, as can easily be shown by preliminary experiment). A solution of 106 g (0.52 mole) of (−)-3-aminomethylpinane hydrochloride ($[\alpha]_D^{22} = -42.8°$, 1% in methanol) in 450 ml of water is then run in over two minutes and the mixture, which is now at 50° C, is stirred further whilst slowly cooling to room temperature. In the course thereof, (−)-3-aminomethylpinane L-pantoate precipitates as a white crystal paste, which is filtered off and rinsed with twice 150 ml of water.

40% strength sodium hydroxide solution is added dropwise to the combined filtrates until the pH is 13. Traces of unreacted (−)-3-aminomethylpinane are extracted with twice 75 ml of methylene chloride.

The filtrate is now brought to pH 1 by adding concentrated sulfuric acid and is concentrated on a rotary evaporator under reduced pressure (from a waterpump) until the inorganic salts begin to crystallize. During this operation, the D-pantoic acid liberated from the sodium D-pantoate cyclizes to D-pantolactone and can be isolated by extraction with methylene chloride (2 × 150 ml, 3 × 100 ml). The methylene chloride is distilled off, giving 66.8 g of D-(−)-pantolactone, $[\alpha]_D^{22} = -42.3°$ (1% in water). The crude lactone is recrystallized from 85 ml of diisopropyl ether, giving 53.4 g (82%) of pure D-(−)-pantolactone, melting point 91°–92°0 C, $[\alpha]_D^{22} = -51.6°$ (1% in water).

The crystalline (−)-3-aminomethylpinane L-pantoate is suspended in 200 ml of water and the pH is brought to 13 by adding 40% strength aqueous sodium hydroxide solution. The (−)-3-aminomethylpinane liberated first separates out as the upper phase and after adding 150 ml of methylene chloride can be run off as the lower phase. The remainder is extracted twice more with 50 ml of methylene chloride, the solutions containing the amine are combined and the dissolved (−)-3-aminomethylpinane is taken up in an equivalent amount of 1 N hydrochloric acid (pH 5.4). The aqueous phase contains 102.8 g (97%) of the (−)-3-aminomethylpinane hydrochloride employed and can, after replenishing with 3.2 g of the resolving reagent, be employed direct for a further diastereomer separation, using the same size of batch as before.

The pH of the aqueous alkaline sodium L-pantoate solution is brought to 1 with concentrated sulfuric acid. The solution is left to stand at room temperature for 1 hour and the pantolactone formmed is then extracted with methylene chloride (2 × 150 ml, 3 × 100 ml). The methylene chloride phases are combined and the solvent is stripped off on a rotary evaporator. 68.8 g of crude L-pantolactone, $[\alpha]_D^{22} = +43.6°$ (1% in water) are left; after heating this material with 56 g of 50% strength sodium hydroxide solution to 133° for two hours, the product no longer shows any optical rotation.

This racemized product can be used without further purification, together with the DL-pantolactone obtained from the mother liquor of the recrystallization from diisopropyl ether (9 g, $[\alpha]_D^{22} = -4°$, 1% in methanol), and after making up the quantity with fresh DL-pantolactone, in the next diastereomer separation batch.

The resolution of racemic pantolactone with (−)-3-aminomethylpinane is repeated nine times, using the method described. In the course of this sequence, the optical purity of the crude D-(+)-pantolactone and of the recycled (−)-3-aminomethylpinane hydrochloride remain constant, within the limits of error. The losses of DL-pantolactone and (−)-3-aminomethylpinane hydrochloride are respectively about 3.3% and 3.1%, per separation, and show no tendency to rise.

EXAMPLE 7

130 g (1 mole) of DL-pantolactone is converted to an aqueous sodium pantoate solution of pH 8.8 in a 2-1 four-necked flask equipped with a stirrer, reflux condenser, thermometer and 500 ml dropping funnel, using the method described in Example 4. The solution is then cooled to 50° and a solution of 106 g (0.52 mole) of (−)-3-aminomethylpinane hydrochloride ($[\alpha]_D^{22} = 43.1°$, 1% in methanol) in 450 ml of 50% strength aqueous methanol is added dropwise in the course of about two minutes. After a few minutes, white crystals of (−)-3-aminomethylpinane L-pantoate form; these are filtered off after stirring for two hours and are rinsed with twice 150 ml of water.

The filtrate and the wash water are combined, brought to pH 13 by adding 40% strength sodium hydroxide solution dropwise, and extracted with twice 75 ml of methylene chloride. The methylene chloride extracts contain approx. 8 g of (−)-3-aminomethylpinane.

The aqueous methanolic solution is brought to pH 1 with concentrated sulfuric acid and concentrated on a rotary evaporator under reduced pressure (from a waterpump) until the inorganic salts begin to crystallize. Under these conditions, the D-pantoic acid liberated from the sodium D-pantoate cyclizes to D-(−)-pantolactone, which is isolated by extraction with methylene chloride (2 × 150 ml, 3 × 100 ml). On distilling off the methylene chloride, 64.9 g of D-(−)-pantolactone of optical rotation $[\alpha]_D^{22} = 44.6°$ (1% in water) are obtained.

The crude lactone is dissolved in 85 ml of warm diisopropyl ether. The solution is seeded with a trace of D-(−)-pantolactone and is allowed to cool slowly to +10° C; 54.5 g (84%) of pure D-(−)-pantolactone of optical rotation $[\alpha]_D^{22} = -51.5°$ (1% in water) are obtained.

The crystalline (−)-3-aminomethylpinane L-pantoate is then treated as described in Example 4. The methylene chloride extracts of (−)-3-aminomethylpinane are combined and 1 N aqueous hydrochloric acid is added until the pH of the aqueous phase is 5.4. This aqueous solution contains 101.7 g (96%) of the optically active base initially employed, in the form of the hydrochloride, and can, after supplementing with 4.3 g of fresh (−)-3-aminomethylpinane hydrochloride, be used, without additional purification, for the next racemate resolution batch.

From the aqueous alkaline sodium L-pantoate solution, 69.2 g of crude L-(+)-pantolactone ($[\alpha]_D^{22} = +45.8°$, 1% in water) can be obtained analogously to Example 4; after heating for two hours with 56 g of 50% strength aqueous sodium hydroxide solution to 133°, the product no longer shows any optical rotation. The strongly alkaline sodium DL-pantoate solution is mixed with 62 of fresh DL-pantolactone and then heated to 80° for 20 minutes, whereupon the pH assumes a value of 8.9; the mixture can be used in this form for the next diastereomer separation batch.

We claim:
1. A process for resolving racemic pantolactone which comprises adding (−)-3-aminomethylpinane or (+)-3-aminomethylpinane or any one of their acid addition salts to a solution of an alkali metal salt of D,L-pantoic acid at temperatures from 0° to 90° C, separating the precipitated crystalline diastereomeric salt, resolving the diastereomeric salt of the D-pantoic acid with alkali metal hydroxide, separating the (+)-or (−)-3-aminomethylpinane and regenerating the D-pantolactone with an acid.

2. A process as claimed in claim 1 wherein the molar ratio of 3-aminomethylpinane addition salt to pantoic acid salt is from 0.5:1 to 0.7:1.

* * * * *